(12) United States Patent
Ingemann

(10) Patent No.: US 6,488,942 B1
(45) Date of Patent: Dec. 3, 2002

(54) DISINFECTING AGENT

(75) Inventor: Knut Ingemann, Bendestorf (DE)

(73) Assignee: DDG Dental Devices GmbH, Bendestorf (DE)

( * ) Notice: Subject to any disclaimer, the term of this patent is extended or adjusted under 35 U.S.C. 154(b) by 0 days.

(21) Appl. No.: 09/529,686

(22) PCT Filed: Oct. 15, 1998

(86) PCT No.: PCT/DE98/03084

§ 371 (c)(1),
(2), (4) Date: Apr. 17, 2000

(87) PCT Pub. No.: WO99/20228

PCT Pub. Date: Apr. 29, 1999

(30) Foreign Application Priority Data

Oct. 18, 1997 (DE) .......................... 197 46 205
Feb. 23, 1998 (DE) .......................... 198 07 433

(51) Int. Cl.$^7$ .......................... A61K 7/22; A61K 7/16; A46B 11/00

(52) U.S. Cl. .......................... 424/401; 424/54; 15/104.94; 15/167.1; 206/209.1

(58) Field of Search .......................... 424/49–58, 401; 206/209.1

(56) References Cited

U.S. PATENT DOCUMENTS

| | | | | | |
|---|---|---|---|---|---|
| 4,473,152 A | * | 9/1984 | Juma et al. | ............... | 206/209.1 |
| 4,585,119 A | * | 4/1986 | Boyington | ............... | 206/209.1 |
| 4,748,158 A | | 5/1988 | Biermann et al. | | |
| 4,900,721 A | * | 2/1990 | Bansemir et al. | ............... | 424/49 |
| 4,911,927 A | * | 3/1990 | Hill et al. | ................... | 424/443 |
| 4,915,219 A | * | 4/1990 | Ottimo | .................... | 206/209.1 |
| 4,915,934 A | * | 4/1990 | Tomlinson | .................... | 424/45 |
| 4,981,678 A | * | 1/1991 | Tomlinson | .................... | 424/45 |
| 5,000,867 A | * | 3/1991 | Heinhuis et al. | ............ | 252/106 |
| 5,086,916 A | * | 2/1992 | Gray | ....................... | 206/209.1 |
| 5,098,711 A | * | 3/1992 | Hill et al. | ................... | 424/401 |
| 5,107,987 A | * | 4/1992 | Palazzoco et al. | ....... | 206/209.1 |
| 5,276,935 A | * | 1/1994 | Lemon et al. | ............ | 15/104.94 |
| 5,340,581 A | * | 8/1994 | Tseng et al. | ................. | 424/401 |
| 5,373,599 A | * | 12/1994 | Lemon et al. | ............ | 15/104.94 |
| 5,376,686 A | * | 12/1994 | Ishikawa et al. | ............ | 514/635 |
| 5,377,824 A | * | 1/1995 | Seymour | ................... | 206/209.1 |
| 5,566,823 A | * | 10/1996 | Summers | .................. | 206/209.1 |
| 5,633,083 A | * | 5/1997 | Iwai et al. | .................... | 428/378 |
| 5,723,132 A | * | 3/1998 | Tseng et al. | ................. | 424/401 |
| 5,776,430 A | * | 7/1998 | Osborne et al. | ............... | 424/43 |
| 5,836,769 A | * | 11/1998 | Spencer | ....................... | 433/216 |
| 5,851,551 A | * | 12/1998 | Tseng et al. | ................. | 424/486 |
| 5,891,422 A | * | 4/1999 | Pan et al. | ...................... | 424/49 |
| 5,906,808 A | * | 5/1999 | Osborne et al. | ............... | 424/43 |
| 5,945,087 A | * | 8/1999 | Nelson et al. | ................. | 424/49 |
| 5,945,088 A | * | 8/1999 | Delli Santi et al. | ........... | 424/49 |
| 6,235,267 B1 | * | 5/2001 | Delli Santi et al. | ........... | 424/49 |
| 6,245,321 B1 | * | 6/2001 | Nelson et al. | ................. | 424/79 |
| 6,261,540 B1 | * | 7/2001 | Nelson | ......................... | 424/53 |

FOREIGN PATENT DOCUMENTS

| | | |
|---|---|---|
| EP | 0 244 363 A1 | 11/1987 |
| EP | 0 363 748 A2 | 4/1990 |
| WO | WO 85/01876 | 5/1985 |
| WO | WO 87/05501 | 9/1987 |
| WO | WO 95/12395 | 5/1995 |
| WO | WO 97/13495 | 4/1997 |

OTHER PUBLICATIONS

Caudry et al J. Canad. Dental Ass. 61(6):511–516 Contamination Toothbrushes and Their Disinfection 20 Minute Soak in Listerine Disinfects Toothbrushes, Jun. 1995.*

Nelson Filho et al Pediatric Denistry 22(5):381–384 Microbial Contamination of Toothbrushes & Their Decontamination 20 Hour Soak of Toothbrushes in 0.129, Cheoritoxioine Gluconate Disinfects (100% Inavbiron), Sep. Oct. 2000.*

Grewal et al J Indian Soc. Pedodorics, Prev. Dent. 14(1): 10–13 Toothbrush Contamination. Effect of Various Disinfecting Solutions 30 Minute Soak in Hexadine (Chorhexidine Gluconate)0.2% or Reach (CPC)10 Minute Soak in Listerine Mouthwash or Hydrogen Brochure, Mar. 1996.*

* cited by examiner

*Primary Examiner*—Shep K. Rose
(74) *Attorney, Agent, or Firm*—Madan, Mossman & Sriram, P.C.

(57) ABSTRACT

This invention concerns a disinfectant composition containing chlorophenyl biguanide and/or chlorobenzyl biguanide compounds and benzoic acid or the salts thereof in an aqueous alcoholic solution and use thereof in the dental field.

22 Claims, No Drawings

DISINFECTING AGENT

PRIORITY INFORMATION

This application is a §371 of PCT/DE98/03084 filed Oct. 15, 1998, based on German Application No. 197 46 205.7 filed Oct. 18, 1997, and German Application No. 198 07 433.6 filed Feb. 23, 1998.

This invention concerns a disinfectant composition containing chlorophenyl biguanide and/or chlorobenzyl biguanide compounds and benzoic acid or the salts thereof in an aqueous alcoholic solution, and it concerns their use in the dental field in particular.

Use of biguanide compounds such as chlorhexidine as disinfectants is essentially known. Chlorhexidine (1,1'-hexamethylenebis[5-(4-chlorophenyl)biguanide] or N,N"-bis(4-chlorophenyl)-3,12-diimino)-2,4,11,13-tetra-azatetra-decanediimidamide is a disinfectant with the following structure which also has an antiseptic effect in the oral cavity:

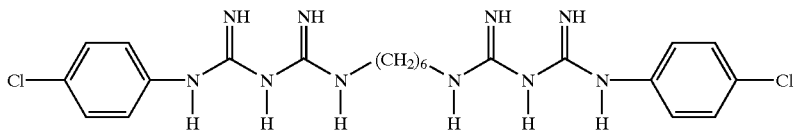

Chlorhexidine has strongly basic groups with a guanidine structure. It has a very low toxicity and is tolerated well even by the mucous membranes. In addition, various derivatives of chlorhexidine are known. Examples include the diacetate, the digluconate and the hydrochloride. The diacetate is known to be soluble in water. In addition, it is also known from European Patent No. 185,971 that the antimicrobial activity of biguanide compounds against gram-positive bacteria is increased by the presence of alkyl glycoside surfactants.

International Patent WO 87/05501 discloses a mouthwash containing a salt of benzoic acid and chlorhexidine gluconate in an aqueous ethanolic solution. However, the composition disclosed there is not stable in storage and it does not have the property which a disinfectant must have if it is to be used for disinfecting toothbrushes or other objects outside the oral cavity.

The object of the present invention is to provide a disinfectant for use outside the oral cavity in the dental field, but at the same time it must have excellent fungicidal, bactericidal and virucidal effects, a short-term microbiocidal activity, a broad spectrum of effect, a low toxicity, no effects on the material of the objects to be disinfected and it should also be stable in storage.

This object is surprisingly achieved according to this invention by a disinfectant composition with a pH of 5 to 9, especially 5 to 8, containing:
a) 0.001 to 4 wt %, preferably 0.01 to 2 wt %, especially 0.6 to 2 wt %, based on the free base, one or more chlorophenyl biguanide and/or chlorobenzyl biguanide compounds,
b) 0.005 to 7 wt %, preferably 0.01 to 3 wt %, especially 0.5 to 3 wt %, based on the free acid, benzoic acid and/or a salt of benzoic acid, and
c) more than 25 wt %, preferably more than 35 wt %, especially 35 to 95 wt % or 35 to 75 wt % of a $C_2$ to $C_4$ alcohol, and d) water, preferably 0.5 to 65 wt %, especially 25 to 65 wt % water.

In addition, the disinfectant composition may also contain, independently of one another:
e) 0.01 to 8 wt %, preferably 0.05 to 6 wt %, especially 1.0 to 5 wt % nonionic surfactants,
f) 0.01 to 5 wt %, preferably 1 to 5 wt % essential oils or fruit flavorings, in particular 0.02 to 4 wt % or 2 to 4 wt % thymol and/or menthol, and
g) 0 to 3 wt % sweeteners.

The following disinfectant composition has proven especially effective for small use quantities of chlorophenyl biguanide and/or chlorobenzyl biguanide compounds:
a) 0.001 to less than 0.1 wt %, based on the free base, of one or more chlorophenyl biguanide and/or chlorobenzyl biguanide compounds;
b) 0.005 to less than 0.1 wt %, based on the free acid, benzoic acid or a salt of benzoic acid;
c) 35 to 65 wt % of the alcohol; and
d) 35 to 65 wt % water.

Essential oils and fruit flavorings according to the present invention include, for example, menthol, thymol, eucalyptol, anethole, carvone, cineole [eucalyptol], eugenol, cinnamaldehyde, caryophyllene, geraniol, citronellol, linalool, salvene, thymol, terpinene, methylchavicol, methyl salicylate, mentyl acetate, vanillin, ionone, linalyl acetate, rhodinol, piperitone or mixtures thereof, in particular menthol or thymol. The composition preferably contains menthol.

Suitable sweeteners include, for example, saccharine sodium (sodium salt of 1,2-benzisothiazol-3(2H)-one 1,1-dioxide, sodium salt of benzosulfimide), cyclamates, acesulfame potassium, aspartame [NutraSweet®], glycerol, sorbitol, mannitol and xylitol, preferably those without any cariogenic action.

The surfactant contained in the disinfectant solution is preferably an alkyl glycoside or an alkenyl glycoside, an alkoxylated alcohol, an alkoxylated carboxylic acid, a sorbitan ester, a polyethoxylated derivative of a sorbitan ester (in particular the commercial products Tween® and Span®), a polyglycerol ester, a sucrate (fatty acid ester of sucrose), an ester of fatty acid with a polyalcohol and/or a polyalkylene glycol. The surfactant may be an alkyl glycoside in particular.

The preferred alkyl and alkenyl glycosides are derived from fatty alcohols and from sugar molecules (ring structure or any other structure) and have glucose or maltose units in particular, optionally with glycosidic bonds, and an average molecular weight of 250 to 1000 g/mol, preferably 300 to 500 g/mol, and at least one hydrocarbon residue with 6 to 20 carbon atoms, preferably 8 to 16 carbon atoms.

The alkyl and alkenyl glycosides may be oligomers, with the glycoside content consisting of 1 to 3 glycoside units on the average, preferably 1 to 2 glycoside units. The alkenyl glycosides may have one or two double bonds.

A typical monoglycoside in the present context would be, for example

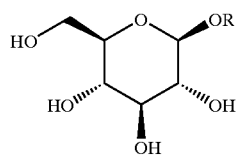

$C_8$–$C_{16}$-alkyl-β-D-glucopyranoside ($C_6H_{11}O_6R$)

Alkyl glycosides used according to this invention include, for example, the commercial products Plantacare® from Henkel KGaA (e.g., grade 818 UP containing 50% active substance and 3–5% polyglucose in aqueous dispersion, neutralized with an organic acid such as acetic acid).

The disinfectant composition is preferably adjusted to a pH of approximately 7. Other known additives such as thickeners, preservatives, coloring agents, antioxidants, perfumes, taste enhancers, fluoride ions, donors, foaming agents, etc. may also be present in the composition.

For example, it may be advantageous to use the disinfectant composition in the form of a gel, foam or spray. Such a composition would then contain, in addition to the disinfectant described above, 10 to 90 wt %, preferably 20 to 60 wt % of a blowing agent such as dimethyl ether, carbon dioxide, propane, butane or a halohydrocarbon such as a fluorochlorocarbon or a fluorocarbon or 0.1 to 10 wt %, preferably 0.2 to 2 wt % of a thickener (gelation agent) such as cellulose or chemically modified cellulose derivatives such as hydroxypropylcellulose, hydroxyethylcellulose or water-soluble salts of cellulose ethers, biologically engineered polysugars (such as xanthenes), polyvinyl alcohols, copolymers of maleic acid with vinyl monomers, polyacrylic acid or the salts thereof, polyarylamides, Carbopol® or cationic polymers such as flotation aids.

Toothbrushes are used in the oral cavity for cleaning teeth. The mechanical cleaning effect of a toothbrush is usually reinforced by dental care products to prevent a buildup of food residues and bacteria in the oral cavity as much as possible. Dental care products such as toothpaste may contain disinfectants. Use of disinfectants in mouthwash preparations is also known. The constant action of disinfectant measures when bactericidal agents are used in oral care products may weaken the physiological oral flora. The disinfectant composition according to this invention is also designed for use outside the oral cavity with regard to its composition. Then there can be no weakening of the oral flora in accordance with this use.

The disinfectant composition according to this invention is preferably used for disinfection of objects which are used in the oral cavity, e.g. for tooth care. Objects of this type include for example toothbrushes, dental picks, dental braces, dental splints, tooth guards, devices for washing out the mouth (spray jets or dental prostheses). These objects are exposed to bacteria, viruses or fungi in the oral cavity in the process of cleaning the teeth and are often cleaned inadequately with water after use. This cleaning is inadequate from a microbiological standpoint in particular. Toothbrushes, for example, can be an ideal culture medium for bacteria and fungi when they are left to stand for several hours at room temperature after a cleaning and then are used again. Viruses may remain infectious for several days. The disinfectant composition is used to particular advantage in a device according to International Patent WO 98/01054.

The efficacy of the disinfectant composition for the above-mentioned applications has been demonstrated on the basis of various microbiological tests. The concentrations given are each based on the active ingredient.

EXAMPLES

| Disinfectant Composition: | wt % |
|---|---|
| Chlorhexidine diacetate | 1.50 |
| Benzoic acid | 2.00 |
| Thymol, DAB 10 [German Pharmacopoeia, 10th edition] | 0.10 |
| Menthol DAB 10 [German Pharmacopoeia, 10th edition] | 3.00 |
| Sodium sucrate | 0.30 |
| Lauryl polyglycoside neutralized with acetic acid | 2.00 |
| Ethanol | 47.21 |
| Purified water | 43.89 |

Microbiological Test

The disinfectant composition was tested with regard to its bactericidal and fungicidal activity to determine whether this disinfectant composition is suitable as a solution for practical use.

Therefore, preservative tests were performed with *Candida albicans*, among other microorganisms. The preservative test did not show any growth of *Candida albicans* after 24 hours. Test organisms according to ATCC that were used were as follows: *Pseudomonas aeruginosa* and *Candida albicans*. To do so, the toothbrushes were wetted with a microbial concentration of $10^5$ and then sprayed with two sprays of the disinfectant composition. The toothbrushes were washed in peptone water after 15, 30 and 60 minutes of exposure time, and then the water was filtered. Next, the filter was incubated for 24 hours on TSG agar. No growth of microorganisms was observed after 15 minutes or after 30 or 60 minutes in the case of *Pseudomonas aeruginosa* Table 2.

In the case of *Candida albicans*, growth was still observed after 15 and 30 minutes, but after exposure to the disinfectant composition for 60 minutes, the growth of only two colonies was observed in the specimens sprayed with the disinfectant composition.

Thus, this yields a definite reduction by at least four logarithmic increments. Further testing against a variety of microorganisms was also performed with the disinfectant composition. To do so, ATCC strains of the species Staph. aureus, *Candida albicans*, hemolytic streptococci of group B, *Klebsiella pneumoniae* were also tested. To do so, the toothbrushes were again wetted with a microbial concentration of $10^5$ and provided with two sprays of the mouthwash 11. The exposure time to the mouthwash here was standardized at 15 minutes, 30 minutes, 60 minutes, two hours and four hours.

Here again, the toothbrushes were rinsed in peptone water, the solution was passed through a sterile filter and then incubated on TSD Aga for 24 hours. It is found that the fungus concentrations were very isolated but still detectable after 60 minutes. However, the microbe concentrations with the other species could no longer be cultured after 60 minutes at the latest. The beta-hemolytic streptococci could no longer be cultured after just five minutes of exposure. *Klebsiella pneumoniae* was also incapable of reproducing after 60 minutes.

The microbiological tests conducted here show that the disinfectant solutions are suitable for eliminating bacteria, fungi and viruses after a suitable treatment time. Testing with the disinfectant compositions with various treatment times revealed that the microorganisms in the disinfectant container for toothbrushes were killed after a standing time of 60 minutes.

Experience has shown that Candida is more resistant and can be reduced within 60 minutes from a log level of $10^5$ to <$10^1$. The results presented in the table were obtained without exposing the toothbrushes previously to a toothpaste with a bacteriostatic action. This disinfectant composition is suitable for adequately disinfecting a toothbrush contaminated with bacteria. In most cases a standing time of only 5 to 30 minutes is sufficient to reduce the microorganisms by at least 3 log levels.

Comparative examples without the use of benzoic acid have shown that the fungicidal effect of the disinfectant composition is greatly reduced and the composition cannot be used for effective disinfection of toothbrushes.

The following disinfectant compositions A and B containing essentially the following ingredients have proven effective for disinfection of toothbrushes:

|                    | (A) Wt % | (B) Wt % |
|--------------------|----------|----------|
| Chlorhexidine base | 0.02     | 0.03     |
| Benzoic acid       | 0.03     | 0.03     |
| Ethanol            | 52       | 48       |

Remainder purified water, surfactants and other additives.

What is claimed is:

1. A disinfectant composition for objects to be introduced into an oral cavity more than once, comprising:
    (a) 0.01 to 2 wt % of a biguanide compound selected from the group consisting of chlorophenyl biguanide compounds and chlorobenzyl biguanide compounds, based on the free base;
    (b) 0.005 to 7 wt % of a benzoic acid compound selected from the group consisting of benzoic acid and a salt of benzoic acid, based on the free acid;
    (c) at least 35 wt % of a $C_2$ to $C_4$ alcohol;
    (d) water; and
    (f) 0.01 to 5 wt % of a compound selected from the group consisting of essential oils and fruit flavorings, wherein the essential oil and fruit flavorings comprise at least one compound selected from the group consisting of thymol, menthol, and mixtures thereof,
where the composition is stable in storage.

2. The disinfectant composition of claim 1 where the biguanide compound is a chlorophenyl biguanide compound selected from the group consisting of chlorhexidine and a chlorhexidine salt.

3. The disinfectant composition of claim 2 where the chlorophenyl biguanide compound is a chlorhexidine salt selected from the group consisting of chlorhexidine diacetate and chlorhexidine digluconate.

4. The disinfectant composition of claim 1 further comprising a parameter independently selected from the group consisting of:
    (c) at least 35 wt % of a $C_2$ to $C_4$ alcohol; and
    (d) 0.5 to 65 wt % water.

5. The disinfectant composition of claim 1 further comprising:
    (a) 0.6 to 2 wt % of biguanide compound selected from the group consisting of chlorhexidine diacetate and chlorhexidine digluconate;
    (b) 0.01 to 3 wt % of the benzoic acid compound;
    (c) 25 to 75 wt % of the alcohol; and
    (d) 25 to 70 wt % water.

6. The disinfectant composition of claim 1 further comprising:
    (g) up to 3 wt % of at least one sweetener.

7. The disinfectant composition of claim 1 further comprising:
    (f) 0.02 to 4 wt % of an essential oils and fruit flavorings compound selected from the group consisting of thymol and menthol.

8. The disinfectant composition of claim 1 further comprising:
    (e) 0.01 to 8 wt % of one or more nonionic surfactants.

9. The disinfectant composition of claim 8 where the (e) surfactant is selected from the group consisting of an alkyl glycoside, an alkenyl glycoside, an alkoxylated alcohol, an alkoxylated carboxylic acid, a sorbitan ester, a polyethoxylated derivative of a sorbitan ester, a polyglycerol ester, an ester of a fatty acid with a polyalcohol and a polyalkylene glycol.

10. The disinfectant composition of claim 1 further comprising:
    (e) 1 to 3 wt % of surfactant selected from the group consisting of an alkyl glycoside and an alkenyl glycoside;
    (f) 2 to 4 wt % of an essential oils and fruit flavorings compound selected from the group consisting of thymol and menthol.

11. The disinfectant composition of claim 8 where the (e) surfactant is selected from the group consisting of an alkyl glycoside and an alkenyl glycoside, where the surfactant has an average molecular weight of 250 to 1000 g/mol and has at least one hydrocarbon residue of from 6 to 20 carbon atoms.

12. The disinfectant composition of claim 1 where the composition has a pH of from 5 to 8.

13. The disinfectant composition of claim 1 where the alcohol (c) is selected from the group consisting of ethanol, n-propanol, and isopropanol.

14. The disinfectant composition of claim 1 further comprising:
    (f) 2 to 4 wt % of menthol as an essential oils and fruit flavorings compound.

15. The disinfectant composition of claim 1 further comprising an additional component selected from the group consisting of 10 to 90 wt % of a blowing agent and 0.1 to 10 wt % of a thickener.

16. Objects introduced into an oral cavity more than once for the purpose of dental care, dental prostheses or oral hygiene wetted with a disinfectant composition comprising:
    (a) 0.01 to 2 wt % of a biguanide compound selected from the group consisting of chlorophenyl biguanide compounds and chlorobenzyl biguanide compounds, based on the free base;
    (b) 0.005 to 7 wt % of a benzoic acid compound selected from the group consisting of benzoic acid and a salt of benzoic acid, based on the free acid;
    (c) at least 25 wt % of a $C_2$ to $C_4$ alcohol;
    (d) water; and
    (f) 0.01 to 5 wt % of a compound selected from the group consisting of essential oils and fruit flavorings, wherein the essential oil and fruit flavorings comprise at least one compound selected from the group consisting of thymol, menthol, and mixtures thereof,
where the composition is stable in storage;
where the objects are selected from the group consisting of tooth care objects, toothbrushes, dental picks, dental braces, dental splints, tooth guards, spray jet devices for washing out the mouth and dental prostheses; and where the objects are wetted for at least 30 minutes.

17. A method of disinfecting objects introduced into an oral cavity more than once for the purpose of dental care, dental prostheses or oral hygiene, comprising:
(i) providing a disinfectant composition, comprising
   (a) 0.01 to 2 wt % of a biguanide compound selected from the group consisting of chlorophenyl biguanide compounds and chlorobenzyl biguanide compounds, based on the free base;
   (b) 0.005 to 7 wt % of a benzoic acid compound selected from the group consisting of benzoic acid and a salt of benzoic acid, based on the free acid;
   (c) at least 25 wt % of a $C_2$ to $C_4$ alcohol;
   (d) water; and
   (f) 0.01 to 5 wt % of a compound selected from the group consisting of essential oils and fruit flavorings, wherein the essential oil and fruit flavorings comprise at least one compound selected from the group consisting of thymol, menthol, and mixtures thereof,
where the composition is stable in storage; and
(ii) wetting the objects with the disinfectant composition for an effective period of time, wherein the effective period of time is at least 30 minutes, and wherein the objects are selected from the group consisting of tooth care objects, toothbrushes, dental picks, dental braces, dental splints, tooth guards, spray jet devices for washing out the mouth and dental prostheses.

18. The method of claim 17 where in providing the disinfectant composition the biguanide compound is a chlorophenyl biguanide compound selected from the group consisting of chlorhexidine and a chlorhexidine salt.

19. The method of claim 17 where in providing the disinfectant composition, the composition further comprises:
   (a) 0.6 to 2 wt % of biguanide compound selected from the group consisting of chlorhexidine diacetate and chlorhexidine digluconate;
   (b) 0.01 to 3 wt % of the benzoic acid compound;
   (c) 25 to 75 wt % of the alcohol; and
   (d) 25 to 70 wt % water.

20. The method of claim 17 where in providing the disinfectant composition, the composition further comprises:
   (e) 0.01 to 8 wt % of one or more nonionic surfactants selected from the group consisting of an alkyl glycoside, an alkenyl glycoside, an alkoxylated alcohol, an alkoxylated carboxylic acid, a sorbitan ester, a polyethoxylated derivative of a sorbitan ester, a polyglycerol ester, an ester of a fatty acid with a polyalcohol and a polyalkylene glycol.

21. The objects of claim 16 where the objects are wetted for at least 60 minutes.

22. The method of claim 17 where the effective period of time is at least 60 minutes.

* * * * *